(12) United States Patent
Tiollais et al.

(10) Patent No.: US 6,416,996 B1
(45) Date of Patent: Jul. 9, 2002

(54) NUCLEOTIDE SEQUENCE COMPRISING THE GENOME OF HEPATITIS B VIRUS, NUCLEOTIDE SEQUENCE CODING THE SURFACE ANTIGEN OF THE HEPATITIS B VIRUS, VECTORS CONTAINING THE NUCLEOTIDE SEQUENCES, PROCESS FOR THE PREPARATION THEREOF, AND ANTIGEN OBTAINED THEREBY

(75) Inventors: Pierre Tiollais; Alex Fritsch; Christine Pourcel, all of Paris; Francois Galibert, Saint-Gratien; Patrick Charnay, Boulogne, all of (FR)

(73) Assignees: Institut Pasteur; Institut National de la Sante et de la Recherche Medicale, both of Paris (FR)

( * ) Notice: Subject to any disclaimer, the term of this patent is extended or adjusted under 35 U.S.C. 154(b) by 0 days.

(21) Appl. No.: 08/478,853

(22) Filed: Jun. 7, 1995

Related U.S. Application Data

(60) Continuation of application No. 08/343,878, filed on Nov. 17, 1994, now abandoned, which is a continuation of application No. 08/115,755, filed on Sep. 3, 1993, now abandoned, which is a continuation of application No. 07/798,067, filed on Nov. 27, 1991, now abandoned, which is a continuation of application No. 07/278,335, filed on Dec. 1, 1988, now abandoned, which is a continuation-in-part of application No. 06/785,499, filed on Oct. 8, 1985, now abandoned, which is a continuation-in-part of application No. 06/395,672, filed on Jul. 6, 1982, now abandoned, which is a continuation of application No. 06/104,835, filed on Dec. 18, 1979, now abandoned, application No. 07/278,335, which is a continuation of application No. 07/011,143, filed on Feb. 5, 1987, now abandoned, which is a continuation of application No. 06/563,356, filed on Dec. 20, 1983, now abandoned, which is a division of application No. 06/261,199, filed on Apr. 30, 1981, now Pat. No. 4,428,941.

(30) Foreign Application Priority Data

Dec. 18, 1978 (FR) .............................. 78 35588
Aug. 30, 1979 (FR) .............................. 79 21811
Apr. 22, 1980 (FR) ........................... 80 309039

(51) Int. Cl.[7] .............................................. A61K 39/29

(52) U.S. Cl. ........................... 435/320.1; 435/5; 435/6; 435/254.11; 435/91.1; 536/23.1; 536/23.72; 536/25.3

(58) Field of Search ..................... 435/5, 6, 68.1, 435/69.1, 91.1, 91.4, 172.3, 235.1, 317.1, 320.1, 254.11; 536/23.1, 23.4, 23.72, 25.3

(56) References Cited

U.S. PATENT DOCUMENTS

| | | | |
|---|---|---|---|
| 4,237,224 A | | 12/1980 | Cohen et al. |
| 4,428,941 A | * | 1/1984 | Galibert et al. |
| 4,935,235 A | * | 6/1990 | Rutter et al. |
| 5,196,194 A | * | 3/1993 | Rutter et al. |

OTHER PUBLICATIONS

Galibert et al, Nature, vol. 281, Oct. 25, 1979, pp646–650, "Nucleotide Sequence of the Hepatitis B Virus Genome (Subtype ayw) Cloned in *E. coli*".*
Burrell et al, Nature, vol. 279, May 3, 1979, pp. 43–47, "Expression in *Escherichia coli* of hepatitis B virus DNA Sequences Cloned in Plasmid p BR322".*
Galibert et al, Nature, 281:646–650 (1979).*
Burrell et al., Nature, 279:43–47 (1979).*
Fritsch et al., C.R. Acad. Sci. Paris Ser. D., 287 (16):1453–1456 (1978).
Hruska et al., J. Virol., 21 (2):666–672 (1977).
Summers et al., Biol. Abstr., 66 (12):72159 (1978).
Leder et al., Science, 196:175–177 (1977).
Blumberg, Science, 197:17–25 (1977).
Murray, Molecular Cloning of Recombinant DNA, Academic Press, New York, Scott et al., Editors, 133, 144–146 (1977).
Noyes et al., Cell, 5:301–310 (1975).
Landers et al., J. Virol., 23(2):368–376 (1977).
Robinson, Ann. Rev. Microbiol., 31:357–377 (1977).
Summers et al., Proc. Natl. Acad. Sci. (USA), 72(11):4597–4601 (1975).
Valenzuela et al., Nature 280:815–819 (1979).
Pasek et al., Nature, 282:575–579 (1979).
Charnay et al., Nature, 286:893–895 (1980).
Sninsky et al., Nature, 279:346–348 (1979).
Dubois et al., Proc. Natl. Acad. Sci. (USA), 77:4549–4553 (1980).
Goedell et al., Proc. Natl. Acad. Sci. (USA), 76:106–110 (1979).
Shine et al., Nature, 285:456–461 (1980).
Tiollais et al., Nature, 317:489–495 (1985).

* cited by examiner

*Primary Examiner*—Laurie Scheiner
(74) *Attorney, Agent, or Firm*—Finnegan, Henderson, Farabow, Garrett & Dunner, L.L.P.

(57) ABSTRACT

A process produces DNA corresponding to that of the DNA of the virus of B hepatitis. It comprises cloning in bacteria the latter DNA, previously repaired by means of the corresponding precursor nucleotides in the presence of a polymerase. Vectors contain the cloned DNA in their genomes. The cloned DNA is useful as a probe for detecting the presence of the virus of B hepatitis in biological samples, particularly blood or plasma. Its expression in bacteria provides a hybrid protein containing a protein fragment having vaccinating properties against hepatitis B. Nucleic acid of reduced size and a vector containing the nucleotide sequence of which DNA codes an immunogenic peptide sequence capable of inducing the generation of antibodies to the virus of viral hepatitis B. It comprises totally or partly the sequence of nucleotides represented in FIG. 9A. Application to the production by cloning in a bacterium of an immunogenic protein immunizing against hepatitis B, or application to the obtention of probes for the diagnosis of the presence of Dane particles in the serum.

4 Claims, 14 Drawing Sheets

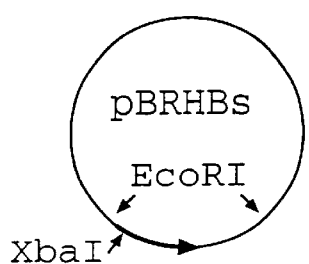
HBV DNA
FIG. 7B
FIG. 7C
FIG. 7D
FIG. 7E
FIG. 7F
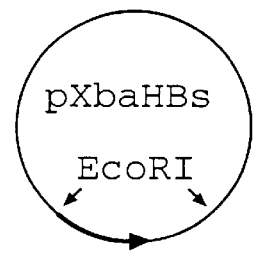
FIG. 7G
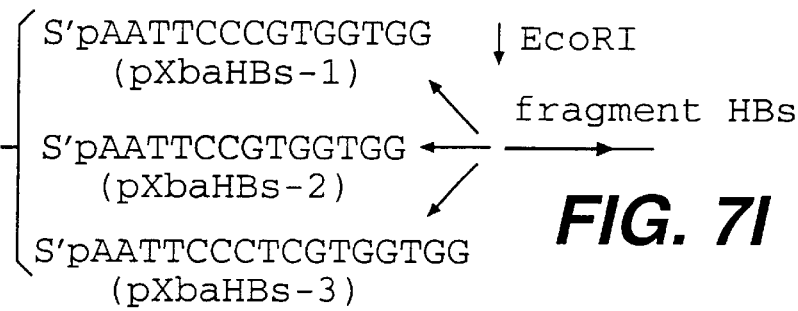
FIG. 7H
FIG. 7I

```
     Ava III(2116)          HhaI(1952)              Hinc II(2191)
     1930       1940       1950       1960       1970       1980
TCGGCAGAGG AGCCGAAAAG GTTCCACGCA TGCGCTGATG GCCCATGACC AAGCCCCAGC
AGCCGTCTCC TCGGCTTTTC CAAGGTGCGT ACGCGACTAC CGGGTACTGG TTCGGGGTCG
     1990       2000       2010       2020       2030       2040
CAGTGGGGT  TGCGTCAGCA AACACTTGGC ACAGACCTGG CCGTTGCCGG GCAACGGGGT
GTCACCCCCA ACGCAGTCGT TTGTGAACCG TGTCTGGACC GGCAACGGCC CGTTGCCCCA
     2050       2060       2070       2080       2090       2100
AAAGGTTCAG GTATTGTTTA CACAGAAAGG CCTTGTAAGT TGGCGAGAAA GTGAAAGCCT
TTTCCAAGTC CATAACAAAT GTGTCTTTCC GGAACATTCA ACCGCTCTTT CACTTTCGGA
     2110       2120       2130       2140       2150       2160
GCTTAGATTG AATACATGCA TACAAAGGCA TCAACGCAGG ATAACCACAT TGTGTAAAAG
CGAATCTAAC TTATGTACGT ATGTTTCCGT AGTTGCGTCC TATTGGTGTA ACACATTTTC
     2170       2180       2190       2200       2210       2220
GGGCAGCAAA ACCCAAAAGA CCCACAATTC GTTGACATAC TTTCCAATCA ATAGGCCTGT
CCCGTCGTTT TGGGTTTTCT GGGTGTTAAG CAACTGTATG AAAGGTTAGT TATCCGGACA
     2230       2240       2250       2260       2270       2280
TAATAGGAAG TTTTCTAAAA CATTCTTTGA TTTTTTGTAT GATGTGTTCT TGTGGCAAGG
ATTATCCTTC AAAAGATTTT GTAAGAAACT AAAAAACATA CTACACAAGA ACACCGTTCC
     2290       2300       2310       2320       2330       2340
ACCCATAACA TCCAATGACA TAACCCATAA AATTTAGAGA GTAACCCCAT CTCTTTGTTT
TGGGTATTGT AGGTTACTGT ATTGGGTATT TTAAATCTCT CATTGGGGTA GAGAAACAAA
```

FIG. 8A

```
     t"s"
        2350           2360           2370           2380           2390           2400
TGTTAGGGTT     TAAATGTATA     CCCAAAGACA     AAAGAAAATT     GGTAACAGCG     GTAAAAGGG
ACAATCCCAA     ATTACACATAT    GGGTTTCTGT     TTTCTTTTAA     CCATTGTCGC     CATTTTTCCC
        2410           2420           2430           2440           2450           2460
ACTCAAGATG     CTGTACAGAC     TTGGCCCCCA     ATACCACATC     ATCCATATAA     CTGAAAGCCA
TGAGTTCTAC     GACATGTCTG     AACCGGGGGT     TATGGTGTAG     TAGGTATATT     GACTTTCGGT
        2470           2480           2490           2500           2510           2520
AACAGTGGGG     GAAAGCCCTA     CGAACCACTG     AACAAATGGC     ACTAGTAAAC     TGAGCCAGGA
TTGTCACCCC     CTTTCGGGAT     GCTTGGTGAC     TTGTTTACCG     TGATCATTTG     ACTCGGTCCT
        2530           2540           2550           2560           2570           2580
GAAACGGGCT     GAGGCCCACT     CCCATAGGAA     TTTTCCGAAA     GCCCAGGATG     ATGGGATGGG
CTTTGCCCGA     CTCCGGGTGA     GGGTATCCTT     AAAAGGCTTT     CGGGTCCTAC     TACCCTACCC
        2590           2600           2610           2620           2630           2640
AATACAGGTG     CAATTTCCGT     CCGAAGGTTT     GGTACAGCAA     CAGGAGGGAT     ACATAGAGGT
TTATGTCCAC     GTTAAAGGCA     GGCTTCCAAA     CCATGTCGTT     GTCCTCCCTA     TGTATCTCCA
        2650           2660           2670           2680           2690           2700
TCCTTGAGCA     GTAGTCATGC     AGGTCCGGCA     TGGTCCCGTG     CTGGTTGTTG     AGGATCCTGG
AGGAACTCGT     CATCAGTACG     TCCAGGCCGT     ACCAGGGCAC     GACCAACAAC     TCCTAGGACC
        2710           2720           2730           2740           2750           2760
AATTAGAGGA     CAAACGGGCA     ACATACCTTG     ATAGTCCAGA     AGAACCAACA     AGAAGATGAG
TTAATCTCCT     GTTTGCCCGT     TGTATGGAAC     TATCAGTCT      TCTTGGTTGT     TCTTCTACTC
        2770           2780           2790           2800           2810           2820
GCATAGCAGC     AGGATGAAGA     GGAAGATGAT     AAAACGCCGC     AGACACATCC     AGCGATAACC
CGTATCGTCG     TCCTACTTCT     CCTTCTACTA     TTTTGCGGCG     TCTGTGTAGG     TCGCTATTGG

FIG. 8B
```

```
2830        2840        2850        2860        2870        2880
AGGACAAGTT  GGAGGACAAG  AGGTTGGTGA  GTGATTGGAG  GTTGGGGACT  GCGAATTTTG
TCCTGTTCAA  CCTCCTGTTC  TCCAACCACT  CACTAACCTC  CAACCCCTGA  CGCTTAAAAC
            2890        2900        2910        2920        2930        2940

GCCAAGACAC  ACGGTAGTTC  CCCCTAGAAA  ATTGAGAGAA  GTCCACCACG  AGTCTAGACT
CGGTTCTGTG  TGCCATCAAG  GGGGATCTTT  TAACTCTCTT  CAGGTGGTGC  TCAGATCTGA
            2950        2960        2970        2980        2990        3000

CTGCGGGTATT GTGAGGATTC  TTGTCAACAA  GAAAAACCCC  GCCTGTAACA  CGAGAAGGGG
GACGCCATAA  CACTCCTAAG  AACAGTTGTT  CTTTTTGGGG  CGGACATTGT  GCTCTTCCCC
            3010        3020        3030        3040        3050        3060

TCCTAGGAAT  CCTGATGTGA  TGTTCTCCAT  GTTCAGCGCA  GGGTCCCCAA  TCGTCGAGAA
AGGATCCTTA  GGACTACACT  ACAAGAGGTA  CAAGTCGCGT  CCCAGGGGTT  AGGAGCTCTT
            3070        3080        3090        3100        3110        3120

GATTGACGAT  AAGGGAGAGG  CAGTAGTCAG  AACAGGGTTT  ACTGTTCCTG  AACTGGAGCC
CTAACTGCTA  TTCCCTCTCC  GTCATCAGTC  TTGTCCCAAA  TGACAAGGAC  TTGACCTCGG
            3130        3140        3150        3160        3170        3180

ACCAGCAGGG  AAATACAGGC  GGGATCTTGC  AGAGTCTTGGT GGAAGGTTGT
TGGTCGTCCC  TTTATGTCCG  CCCTAGAACG  TCTCAAACCA  CCTTCCAACA

GG    L 3'        Hinc II(2963)    p"S"        Hha I(3036)  Ava I(3053)
CC    S 5'
      EcoRI (1/3182)                                              f2↓
```

FIG. 8C

```
                                                                    f2
                                                                    ↓
                                                                    )
                                                       ──────────→
                                                                                      30
     3'   TAC   CTC   TTG   TAG   TGT   AGT   CCT   AAG   GAT   CCT
     5'   ATG   GAG   AAC   ATC   ACA   TCA   GGA   TTC   CTA   GGA
          MET   GLU   ASN   ILE   THR   SER   GLY   PHE   LEU   GLY
                                                                                      60
          GCG   GAA   GAG   CAC   AAT   GTC   CGC   CCC   AAA   AAG
          CCC   CTT   CTC   GTG   TTA   CAG   GCG   GGG   TTT   TTC
          PRO   LEU   LEU   VAL   LEU   GLN   ALA   GLY   PHE   PHE
                                                                                      90
          AAC   AAC   TGT   TCT   TAG   GAG   TGT   TAT   GGC   GTC
          TTG   TTG   ACA   AGA   ATC   CTC   ACA   ATA   CCG   CAG
          LEU   LEU   THR   ARG   ILE   LEU   THR   ILE   PRO   GLN
                                                                                     120
          TCA   GAT   CTG   AGC   ACC   ACC   TGA   AGA   GAG   TTA
          AGT   CTA   GAC   TCG   TGG   TGG   ACT   TCT   CTC   AAT
          SER   LEU   ASP   SER   TRP   TRP   THR   SER   LEU   ASN
                                                                                     150
          AAA   GAT   CCC   CCT   TGA   TGG   CAC   ACA   GAA   CCG
          TTT   CTA   GGG   GGA   ACT   ACC   GTG   TGT   CTT   GGC
          PHE   LEU   GLY   GLY   THR   THR   VAL   CYS   LEU   GLY
                                                                                     180
          GTT   TTA   AGC   GTC   AGG   GGT   TGG   AGG   TTA   GTG
          CAA   AAT   TCG   CAG   TCC   CCA   ACC   TCC   AAT   CAC
          GLN   ASN   SER   GLN   SER   PRO   THR   SER   ASN   HIS
                                                                                     210
          AGT   GGT   TGG   AGA   ACA   GGA   GGT   TGA   ACA   GGA
          TCA   CCA   ACC   TCT   TGT   CCT   CCA   ACT   TGT   CCT
          SER   PRO   THR   SER   CYS   PRO   PRO   THR   CYS   PRO
                                                                                     240
          CCA   ATA   GCG   ACC   TAC   ACA   GAC   GCC   GCA   AAA
          GGT   TAT   CGC   TGG   ATG   TGT   CTG   CCG   CGT   TTT
          GLY   TYR   ARG   TRP   MET   CYS   LEU   ARG   ARG   PHE
```

FIG. 9A

```
                                                              270
TAG  TAG  AAG  GAG  AAG  TAG  GAC  GAC  GAT  ACG
ATC  ATC  TTC  CTC  TTC  ATC  CTG  CTG  CTA  TGC
ILE  ILE  PHE  LEU  PHE  ILE  LEU  LEU  LEU  CYS
                                                              300
GAG  TAG  AAG  AAC  AAC  CAA  GAA  GAC  CTG  ATA
CTC  ATC  TTC  TTG  TTG  GTT  CTT  CTG  GAC  TAT
LEU  ILE  PHE  LEU  LEU  VAL  LEU  LEU  ASP  TYR
                                                              330
GTT  CCA  TAC  AAC  GGG  CAA  ACA  GGA  GAT  TAA
CAA  GGT  ATG  TTG  CCC  GTT  TGT  CCT  CTA  ATT
GLN  GLY  MET  LEU  PRO  VAL  CYS  PRO  LEU  ILE
     Site Bam  HI                                             360
GGT  CCT  AGG  AGT  TGT  TGG  TCG  TGC  CCT  GGT
CCA  GGA  TCC  TCA  ACA  ACC  AGC  ACG  GGA  CCA
PRO  GLY  SER  SER  THR  THR  SER  THR  GLY  PRO
                                                              390
ACG  GCC  TGG  ACG  TAC  TGA  TGA  CGA  GTT  CCT
TGC  CGG  ACC  TGC  ATG  ACT  ACT  GCT  CAA  GGA
CYS  ARG  THR  CYS  MET  THR  THR  ALA  GLN  GLY
                                                              420
TGG  AGA  TAC  ATA  GGG  AGG  ACA  ACG  ACA  TGG
ACC  TCT  ATG  TAT  CCC  TCC  TGT  TGC  TGT  ACC
THR  SER  MET  TYR  PRO  SER  CYS  CYS  CYS  THR
                                                              450
TTT  GGA  AGC  CTG  CCT  TTA  ACG  TGG  ACA  TAA
AAA  CCT  TCG  GAC  GGA  AAT  TGC  ACC  TGT  ATT
LYS  PRO  SER  ASP  GLY  ASN  CYS  THR  CYS  ILE
                                                              480
GGG  TAG  GGT  AGT  AGG  ACC  CGA  AAG  CCT  TTT
CCC  ATC  CCA  TCA  TCC  TGG  GCT  TTC  GGA  AAA
PRO  ILE  PRO  SER  SER  TRP  ALA  PHE  GLY  LYS
```

*FIG. 9B*

```
                                                            510
AAG  GAT  ACC  CTC  ACC  CGG  AGT  CGG  GCA  AAG
TTC  CTA  TGG  GAG  TGG  GCC  TCA  GCC  CGT  TTC
                    Site Hae III
PHE  LEU  TRP  GLU  TRP  ALA  SER  ALA  ARG  PHE
                                                            540
AGG  ACC  GAG  TCA  AAT  GAT  CAC  GGT  AAA  CAA
TCC  TGG  CTC  AGT  TTA  CTA  GTG  CCA  TTT  GTT
SER  TRP  LEU  SER  LEU  LEU  VAL  PRO  PHE  VAL
                                                            570
GTC  ACC  AAG  CAT  CCC  GAA  AGG  GGG  TGA  CAA
CAG  TGG  TTC  GTA  GGG  CTT  TCC  CCC  ACT  GTT
GLN  TRP  PHE  VAL  GLY  LEU  SER  PRO  THR  VAL
                                                            600
ACC  GAA  AGT  CAA  TAT  ACC  TAC  TAC  ACC  ATA
TGG  CTT  TCA  GTT  ATA  TGG  ATG  ATG  TGG  TAT
TRP  LEU  SER  VAL  ILE  TRP  MET  MET  TRP  TYR
                                                            630
ACC  CCC  GGT  TCA  GAC  ATG  TCG  TAG  AAC  TCA
TGG  GGG  CCA  AGT  CTG  TAC  AGC  ATC  TTG  AGT
TRP  GLY  PRO  SER  LEU  TYR  SER  ILE  LEU  SER
                                                            690
GGG  AAA  AAT  GGC  GAC  AAT  GGT  TAA  AAG  AAA
CCC  TTT  TTA  CCG  CTG  TTA  CCA  ATT  TTC  TTT
PRO  PHE  LEU  PRO  LEU  LEU  PRO  ILE  PHE  PHE ACA  GAA  ACC  CAT  ATG  TAA  ATT  5'
TGT  CTT  TGG  GTA  TAC  ATT  TAA  3'
CYS  LEU  TRP  VAL  TYR  ILE  STOP
```

```
                                    2191  2200        2210        2220
                                 5' TTGACATAC  TTTCCAATCA  ATAGGCCTGT
                                 3' AACTGTATG  AAAGGTTAGT  TATCCGGACA 2230        2240           2250        2260        2270        2280
   TAATAGGAAG  TTTTCTAAAA     CATTCTTTGA  TTTTTGTAT   AAAGGTTCT   TGTGGCAAGG
   ATTATCCTTC  AAAAGATTTT     GTAAGAAACT  AAAAAACATA  CTACACAAGA  ACACCGTTCC 2290        2300           2310        2320        2330        2340
   ACCCATAACA  TCCAATGACA     TAACCCATAA  AATTTAGAGA  GTAACCCCAT  CTCTTTGTTT
   TGGGTATTGT  AGGTTACTGT     ATTGGGTATT  TTAAATCTCT  CATTGGGGTA  GAGAAACAAA 2350        2360           2370        2380        2390        2400
   TGTTAGGGTT  TAAATGTATA     CCCAAAGACA  AAAGAAAATT  GGTAACAGCG  GTAAAAAGGG
   ACAATCCCAA  ATTTACATAT     GGGTTTCTGT  TTTCTTTTAA  CCATTGTCGC  CATTTTTCCC 2410        2420           2430        2440        2450        2460
   ACTCAAGATG  CTGTACAGAC     TTGGCCCCCA  ATCCATATAA  ATCCATATAA  CTGAAAGCCA
   TGAGTTCTAC  GACATGTCTG     AACCGGGGGT  TAGGTATATT  TAGGTATATT  GACTTTCGGT 2470        2480           2490        2500        2510        2520
   AACAGTGGGG  GAAAGCCCTA     CGAACCACTG  AACAAATGGC  ACTAGTAAAC  TGAGCCAGGA
   TTGTCACCCC  CTTTCGGGAT     GCTTGGTGAC  TTGTTTACCG  TGATCATTTG  ACTCGGTCCT 2530        2540           2550        2560        2570        2580
   GAAACGGGCT  GAGGCCCACT     CCCATAGGAA  TTTTCCGAAA  GCCCAGGATG  ATGGGATGGG
   CTTTGCCCGA  CTCCGGGTGA     GGGTATCCTT  AAAAGGCTTT  CGGGTCCTAC  TACCCTACCC
```

FIG. 10B

```
2590        2600        2610        2620        2630        2640
AATACAGGTG  CAATTCCGTG  CCGAAGGTTT  GGTACAGCAA  CAGGAGGGAT  ACATAGAGGT
TTATGTCCAC  GTTAAGGCAC  GGCTTCCAAA  CCATGTCGTT  GTCCTCCCTA  TGTATCTCCA
2650        2660        2670        2680        2690        2700

TCCTTGAGCA  GTAGTCATGC  AGGTCCGGCA  TGGTCCCGTG  CTGGTTGTTG  AGGATCCTGG
AGGAACTCGT  CATCAGTACG  TCCAGGCCGT  ACCAGGGCAC  GACCAACAAC  TCCTAGGACC
2710        2720        2730        2740        2750        2760

AATTAGAGGA  CAAACGGGCA  ACATACCTTG  ATAGTCCAGA  AGAACCAACA  AGAAGATGAG
TTAATCTCCT  GTTTGCCCGT  TGTATGGAAC  TATCAGGTCT  TCTTGGTTGT  TCTTCTACTC
2770        2780        2790        2800        2810        2820

GCATAGCAGC  AGGATGAAGA  GGAAGATGAT  AAAACGCCGC  AGACACATCC  AGCGATAACC
CGTATCGTCG  TCCTACTTCT  CCTTCTACTA  TTTTGCGGCG  TCTGTGTAGG  TCGCTATTGG
2830        2840        2850        2860        2870        2880

AGGACAAGTT  GGAGGACAAG  AGGTTGGTGA  GTGATTGGAG  GTTGGGGACT  GCGAATTTTG
TCCTGTTCAA  CCTCCCTGTTC  TCCAACCACT  CACTAACCTC  CAACCCCTGA  CGCTTAAAAC
2890        2900        2910        2920        2930        2940

GCCAAGACAC  ACGGTAGTTC  CCCCTAGAAA  ATTGAGAGAA  GTCCACCACG  AGTCTAGACT
TGCCATCAAG  GGGGATCTTT  TAACTCTCTT  CAGGTGGTGC  TCAGATCTGA
2950        2960

CTGCGGTATT  GTGAGGATTC                          TTG  L  3'
GACGCCATAA  CACTCCTAAG                          AAC  S  5'
```

$\xrightarrow{f_2}$

FIG. 11

| | | | | | | | | | | |
|---|---|---|---|---|---|---|---|---|---|---|
| TRP | THR | 24 ARG | LEU | THR | ILE | PRO | SER | LEU | ASP | SER |
| | | | | | | | | | | 50 TRP |
| GLN | SER | LEU | PHE | LEU | PRO | 30 GLN | THR | VAL | CYS | |
| | | ILE 40 ASN | | | | | | | | GLY |
| PRO | ASN | GLN | PRO | THR | GLY | THR | SER | PRO | THR | 80 CYS |
| ILE | PRO | SER 70 PRO | CYS | GLY | ASN | SER | CYS | ARG | ARG | PHE |
| VAL | THR | CYS | LEU | TYR | ARG | TRP | LEU | ILE | PHE | |
| | | | | | | | | | | 110 LEU |
| PRO | PHE | LEU | PHE | ILE | LEU | LEU | VAL | CYS | LEU | ILE |
| THR | LEU | PHE 100 LEU | GLN | GLY | MET | 90 CYS | CYS | ARG | LEU | |
| LYS | ALA | ASP | TYR | SER | THR | PRO 120 PRO | SER | CYS | CYS | 140 MET |
| TRP | PRO | SER 130 GLY | PHE | SER | MET | | CYS | ILE | PRO | THR |
| SER | ALA | ASP | GLY | CYS | TYR | PRO 150 ILE | PRO | ALA | SER | 170 SER |
| LEU | PHE | GLY 160 LYS | LEU | LEU | TRP | TRP 180 VAL | ALA | SER | ARG | PHE |
| TRP | LEU | SER | VAL | VAL | PRO | ILE | GLN | TRP | VAL | 200 GLY |
| | | LEU 190 VAL | | | | | | | | TYR |
| LEU | SER | THR | TRP | LEU | SER | ILE 210 SER | TRP | MET | MET | |
| TRP | PRO | SER | TYR | SER | ILE | | LEU | PHE | LEU | |
| LEU | GLY | LEU 220 VAL | LEU | LEU | LEU | PRO 226 ILE | TYR | VAL | PRO | LEU |
| LEU | PRO | PHE | PHE | CYS | | | | | | |

FIG. 12

| Codon 1 | Codon 2 | AA |
|---|---|---|
| ACG | TGC | CYS |
| GCC | CGG | ARG |
| TGG | ACC | THR |
| ACG | TGC | CYS |
| TAC | ATG | MET |
| TGA | ACT | THR |
| TGA | ACT | THR |
| CGA | GCT | ALA |
| GTT | CAA | GLN |
| CCT | GGA | GLY |
| TGG | ACC | THR |
| AGA | TCT | SER |
| AGG | TCC | SER |
| AGT | TCA | SER |
| TGT | ACA | THR |
| TGG | ACC | THR |
| TCG | AGC | SER |
| TGC | ACG | THR |
| CCT | GGA | GLY |
| GGT | CCA | PRO |

(position 390 ↑ $f_2$; position 360)

| Codon 1 | Codon 2 | AA |
|---|---|---|
| TTT | AAA | LYS |
| GGA | CCT | PRO |
| AGC | TCG | SER |
| CTG | GAC | ASP |
| CCT | GGA | GLY |
| TTA | AAT | ASN |
| ACG | TGC | CYS |
| TGG | ACC | THR |
| ACA | TGT | CYS |
| GGG | CCC | PRO |
| TAC | ATA | TYR |
| ATG | TAT | MET |
| AGG | TCC | SER |
| ACA | TGT | CYS |
| ACA | TGT | CYS |
| ACG | TGC | CYS |
| ACA | TGT | CYS |
| TGG | ACC | TRP |

(position 420)

| Codon 1 | Codon 2 | AA |
|---|---|---|
| AAG | GAT | PHE |
| GAT | CTA | LEU |
| CTC | GAG | GLU |
| ACC | TGG | TRP |
| TAG | ATC | ILE |
| GGG | ATT | ILE |
| TGG | ACC | THR |
| ACA | TGT | CYS |
| GGT | AGT | SER |
| CCA | TCA | SER |
| AGG | TCC | SER |
| ACC | TGG | TRP |
| CGA | GCT | ALA |
| AAG | TTC | PHE |
| ACA | TGT | CYS |
| TGG | ACC | THR |
| CCT | GGA | GLY |
| TTT | AAA | LYS |

(position 480)

NUCLEOTIDE SEQUENCE COMPRISING THE GENOME OF HEPATITIS B VIRUS, NUCLEOTIDE SEQUENCE CODING THE SURFACE ANTIGEN OF THE HEPATITIS B VIRUS, VECTORS CONTAINING THE NUCLEOTIDE SEQUENCES, PROCESS FOR THE PREPARATION THEREOF, AND ANTIGEN OBTAINED THEREBY

CROSS-REFERENCE TO RELATED APPLICATIONS

This application is a continuation of application Ser. No. 08/343,878, filed Nov. 17, 1994, now abandoned which is a continuation of application Ser. No. 08/115,755, filed Sep. 3, 1993, now abandoned which is a continuation of application Ser. No. 07/798,067, filed Nov. 27, 1991, now abandoned which is a continuation of application Ser. No. 07/278,335, filed Dec. 1, 1988, now abandoned which is a continuation-in-part of application Ser. No. 06/785,499, filed Oct. 8, 1985, now abandoned which is a continuation-in-part of application Ser. No. 06/395,672, filed Jul. 6, 1982, now abandoned, which is a continuation of application Ser. No. 06/104,835, filed Dec. 18, 1979, now abandoned. Application Ser. No. 07/278,335 is also a continuation-in-part of application Ser. No. 07/011,193, filed Feb. 5, 1987, now abandoned, which is a continuation of application Ser. No. 06/563,356, filed Dec. 20, 1983, now abandoned, which is a divisional of application Ser. No. 06/261,199, filed Apr. 30, 1981, issued as U.S. Pat. No. 4,428,941.

BACKGROUND OF THE INVENTION

The invention relates to a process for the production of a DNA (desoxyribonucleic acid) comprising the genome characteristic of that of the B hepatitis virus. It also relates to DNAs of which a fragment is constituted by a double strand DNA corresponding to that of viral B hepatitis. In addition, it relates to vectors and compositions including such DNAs, for taking advantage of their biological properties. The invention relates to a nucleic acid comprising a nucleotide sequence capable of coding an immunogenic peptide sequence corresponding to the surface antigen of the virus of viral hepatitis B, and to the polypeptides and peptides obtained. It relates also to a process enabling such a nucleic acid to be obtained.

B hepatitis is a frequent viral disease, more particularly in tropical Africa, in Southeast Asia, and in the Far East where about 10% of the people are carriers of the surface viral antigen also designated as HBs antigen.

Though the infection is often manifested by an acute form without sequelae, it can also be at the origin of a chronic hepatitis, of cirrhosis, and even of fatal hepatic necrosis. This explains the importance of studies devoted to the biology of the virus, and the recent development of a vaccine whose efficiency has been demonstrated on patients and members of the personnel of hemodialysis centers (Ph. MAUPAS, A. GOUDEAU, P. COURSAGET, J. DRUCKER and Ph. BAGROS, Intervirol., 10, 1978, p. 196–208). The Dane particle (D. S. DANE, C. H. CAMERON and M. BRIGGS, Lancet. i. 1970, p. 695–698) is at present considered as the etiological viral agent. This particle, which can be detected by observation with the electron microscope, has a diameter of 42 nm. The patient's serum in the preicteric phase contains up to $10^9$ or even $10^{10}$ of it per milliliter. It possesses an envelope (Australia antigen or HBs antigen), a capsid (HBc antigen), an endogenic polymerase, and a DNA molecule (J. L. Melnick, G. R. DREESMAN and F. B. HOLLINGER, Sc. Amer., 237, 1977, p. 44–52). Under observation with the electron microscope, the genome appears as a bicatenary DNA ring possessing a monocatenary region, whose length varies from one molecule to the next (J. SUMMERS, A. O'CONNELL and I. MILLIMAN, Proc. Nat. Acad. Sc., 72, 1975, p. 4597–4601), (W. S. ROBINSON, Ann. Rev. Microbiol., 31, 1977). This ring is constituted by two intertwined linear molecules of unequal lengths (as shown diagrammatically in FIG. 1). It is the smallest viral genome known in mammals. The longest strand contains about 3,200 bases. The endogen polymerase DNA can be used to repair in vitro the single strand region ($b_1$ in FIG. 1) of the shortest strand (T. A. LANDERS, H. B. GREENBERG and W. S. ROBINSON, J. Virol., 23, 1977, p. 368–376). All these very special properties of the Dane particle further increase the interest of studying the biology of this virus.

Electrophoretic analysis of the proteins of the envelope has shown the presence of 2 to 7 polypeptides of which the principal are called: polypeptide I and polypeptide II (PETERSON D. L., ROBERS I. M. and VYAS G. N. (1977) Proc. Nat. Acad. Sci., USA, 74 1530–1534, and PETERSON D. L., CHIEN D. Y., VYAS G. N., NITECHKI D., and BOND H. (1978). In Viral Hepatitis, ed. G. VYAS, S. COHEN and R. SCHMID, The Franklin Institute Press, Philadelphia, 569–573).

The Polypeptide I has a weight of 22,000 to 26,000 daltons. Polypeptide II is glycosylated and has a molecular weight of 28,000 to 30,000 daltons. The amino acid composition of these two polypeptides is very similar, the sequences which form, respectively, their 15 first amino acids (from the N-terminal end) and their last 3 amino acids are identical, so that the hypothesis has formulated that polypeptide II could differ from polypeptide I only by a glycosylation. Until now, the sequence of the I and II polypeptides themselves, and the location in the viral DNA of the sequence coding these peptides have not been done.

Study of the virus is, however, at present made particularly difficult by reason of the difficulties of supplies of serum containing Dane particles. Even a rich serum does not permit the preparation of large amounts of DNA (of the order of 1 γ of DNA per volume of 500 ml of serum). It is hence necessary to collect serums of various origins corresponding to several genetic variants (J. P. SOULIER and A. M. COUROUCE-PAUTY, Vox Sang. 25, 1973, p. 212–235), which renders precarious a study of the primary structure of the genome. The presence of the single strand region makes difficult, moreover, the establishment of a physical map by restriction enzymes.

The problem of the isolation of relatively large amounts of viral particles attains a still increased importance, when it is desired to have available sufficient amounts of viral particles, more particularly of their HBs antigens, which appear to carry a surface antigen (protein) having vaccinating properties. The present methods of vaccination, if they have demonstrated their efficiency, are not however absolutely devoid of drawbacks. In particular, preparations of HBs, used as a vaccine, may contain antigen components coming from hepatic cells, which can be the origin of an autoimmune response (B. S. BLUMBERG, Science, 197, 1977, p. 17–24).

Study of the virus is also extremely difficult to the extent that no cell culture system is available enabling the propagation of the virus. This difficulty has already in part been overcome, more particularly as regards the ayw serotype. The whole DNA (genome) of the virus has been identified and cloned, notably in *E. coli*, after its previous insertion in the single EcoRI site of a λ gt. WES. λB vector, according to the technique by FRITSCH A., POURCEL C., CHARNAY P., and TIOLLAIS P. (1978) C. R. Acad. de Paris, 287, 1,453–456).

Until now, the sequence of the I and II polypeptides themselves, and the location in the viral DNA of the sequence coding these peptides have not been done.

It is, therefore, an object of the invention notably to overcome these difficulties, more particularly to provide a process enabling the production of DNA of B hepatitis virus (or of the Dane particle), in sufficient amounts for the realization of the above-mentioned studies, and in a state of purity such that its use can be contemplated, even for therapeutic uses.

It is also an object of the invention to provide a much smaller DNA sequence than the viral DNA itself, containing the sequence adapted to code the peptide sequence endowed with immunogenic properties enabling, when it is introduced into the organism of a living host, to induce the formation by the latter of antibodies capable of protecting this same host subsequently with respect to the virus of viral hepatitis B, notably when the latter is in virulent state.

SUMMARY OF THE INVENTION

The invention takes advantage of the fact that the DNA of the Dane particle possesses, after in vitro "repair" in the presence of precursor nucleotides and of a polymerase, a single recognition site with regard to certain endonucleases, notably restriction enzymes, such as the enzyme EcoRI or Xho.

The process of the invention for producing a DNA comprising the genome characteristic of that of the DNA of the B hepatitis virus is characterized by the cloning in a bacterium of a double strand DNA, formed from the B hepatitis virus DNA, notably after repair of the latter in vitro as indicated above. This double strand DNA will be denoted below as DNA-HVB. Preferably, the polymerase used is endogenous polymerase of the B hepatitis virus itself.

Preferably, the DNA to be cloned has, previously, been cleaved by an endonuclease, such as defined above, notably by the restriction enzyme EcoRI.

The invention stems not only from the complete nucleotide analysis of the genome of the Dane particle, which the inventors have achieved, but to the idea that they have had for identifying the coding gene (called below "S gene") of the abovesaid polypeptides, to search in the complete nucleotide structure thus preestablished of the genome of the Dane particle, for those of the sequences of the nucleotides capable of coding the known proximal and terminal peptide sequences of these polypeptides.

DETAILED DESCRIPTION

To carry out the cloning, recourse is advantageously had to a vector, notably a phage or plasmid, in which the double strand DNA, previously cleaved at its single site, will have first been inserted.

By way of example of a phage enabling the easy cloning of the double strand DNA, first opened by EcoRI, may be mentioned λgtWES. λB (P. LEDER, D. TIEMEIER, and L. ENQUIST, SCIENCE, 196 (1977) pp. 175–177), which only comprises two EcoRI sites (EcoRI λ1 and EcoRI λ2). The latter enable the insertion of the whole of the DNA of the B hepatitis virus in the genome of this phage, instead and in place of the fragment inside this virus and previously situated between these two EcoRI sites.

It is naturally self-evident that any other vector comprising two EcoRI sites, or even a single EcoRI site, in a part unessential for its own replication, may be used for the same purposes.

Thus, the cloning process according to the invention can include the following essential steps:

the repair of the DNA of the B viral hepatitis, in the presence of precursor nucleotides and of a polymerase to form DNA-HVB;

the cleavage of the DNA-HVB by the enzyme selected, notably EcoRI;

the cleavage of the DNA of the vector, recovery of the portions of this DNA (two or three according as the vector includes one or two EcoRI sites), separation and isolation, notably by ultra centrifugation of the two parts of this DNA, which contained in particular, respectively, the head and tail genes of the phage and the replication genes of the phage (the two operations which precede being feasible simultaneously);

the mixing of these two parts of the DNA vector and of the DNA-HVB and their reaction in the presence of DNA-ligase, notably such as T4 DNA-ligase;

the transfection or transformation of a culture of host bacteria by the products obtained; and, after incubation of the culture, the recovery of phages, the extraction of their DNA recombinants, denoted below by λ-HVB1, which then contain DNA-HVB inserted in their genomes and, optionally, the treatment of the latter by the EcoRI enzyme and the isolation notably by ultracentrifugation, of the DNA-HVB, which is detectable by electrophoresis on an agarose gel, due to the fact that it migrates as the slowest fraction and the size of which can then be evaluated at about 3,200 pairs of bases.

Hence, novel products are obtained which are of direct use in several fields. The DNAs thus produced, before or after separation of the DNA-HVB, notably by cleavage with EcoRI, are usable as a probe for the in vitro diagnosis of the presence in biological samples of the B-hepatitis virus. To this end, these DNAs can be marked in any manner known in itself by a radio element. The use of such labeled DNAs is particularly advantageous in that it does not require considerable blood samples in persons in whom the presence of the B hepatitis virus is suspected.

By way of example, the interest which attaches to this use for study of contagious cases of B hepatitis or of the detection of the B hepatitis virus treated in hemodialysis centers, can be stressed. In the same way, this method of diagnosis is suited to the checking of blood samples which are to be involved in blood transfusion (or blood plasma or serum).

The invention also relates, by way of novel product, to the vectors in which a double strand DNA corresponding to that of viral hepatitis is inserted. In another mode of application of the invention, it is possible to induce the expression of the vectors as indicated above, in a bacterium, in order to induce the synthesis of a hybrid protein containing the HBs antigen in particular, for the study and for the preparation of vaccines with regard to B viral hepatitis.

With this in view, it may be advantageous to use as a vector a modified λ bacteriophage comprising in combination:

mutations having the effect of preventing or retarding the expression of the late genes, particularly of regulating the production of the proteins necessary for encapsidation of this modified DNA in a bacterium notably *E. coli*, provided with suppressors of said mutations;

a DNA fragment comprising a part at least of the Z gene of *E. coli* and a promotor of the lactose operon (or of an analogous bacterial operon) inserted in a non-essential part of the genome of the phage; and a site of cleavage by an endonuclease in the above-said part of the Z gene, to the exclusion of any other cleavage site by the same endonuclease in the above-said modified DNA.

Advantageously, the bacterial operon concerned is *E. coli* lactose operon, the mutations of the abovesaid late genes affect the Q and S genes and the single cleavage site is a EcoRI site.

Such a phage is disclosed in "Molec. Gen. Gent." 170, pp. 171–178 (1979).

The manufacture of the above-said hybrid protein containing the protein corresponding to a DNA-HVB can then proceed as follows. It comprises infecting by said modified phage a bacterium, notably *E. coli*, not provided with suppressors of the mutations of the late genes of this phage, causing the bacterial strain, if necessary in the presence of a β-galactosidase inducer, the hybrid protein being then recoverable from the cellular proteins formed.

If necessary, the vector used (whether it relates to the vector identified above by way of example or any other phage or plasmid vector) may be modified to ensure the reading in the correct phase of the DNA-HVB inserted in this vector. This can be carried out notably by resorting to the technique consisting of inserting in the vector concerned either two pairs, or four pairs of supplementary bases between the initiation point of the translation of the DNA fragment whose expression is sought and the first pair of bases of the recognition site proximal to the restriction enzyme, notably EcoRI, which is intended to constitute the linkage between the corresponding part of the vector and the proximal end of the DNA-HVB which must be inserted. The added pairs of bases must naturally be such that there are not introduced into the vector triplets of bases which would form a "nonsense" codon whose effect would be to interrupt the translation. There is thus obtained that the pairs of bases which in the first vector form respectively the first pairs of bases of each of the successively translated codons, become in at least a part of the two other vectors, respectively the second and third pairs (or vice versa) of the codons whose translation will be effected in the same host, previously transfected or transformed by these other vectors. It is thus possible to have a set of vectors enabling the three possible reading phases.

Starting from the first vector including an EcoRI site at a predetermined distance from the initiation point of the translation, it is possible to obtain one of the two other above-indicated vectors, for example by applying the process which comprises:

cutting the first vector by means of the EcoRI enzyme at the level of this site, collecting that of the two phage fragments which comprises the initiation point of the translation, trimming the monocatenary strand of its EcoRI cohesive end by means of a suitable endonuclease, for example S1 endonuclease, recombining the thus modified fragment, at the level of the free end formed with a fragment such as that named "linker" of the formula

which itself possesses a recognition site for the EcoRI restriction enzyme, producing the digestion of the modified vector fragment in the presence of EcoRI, which leads to the production of a vector fragment in which the first pair of bases of the EcoRI cohesive end is from then on shifted by two pairs of additional bases with respect to the position that it occupied previously with respect to the initiation point of the translation, and lastly recombining this thus modified fragment with the other, notably in the presence of a DNA-ligase, notably T4 DNA-ligase.

The operation which has just been described can be repeated a second time to produce an additional similar shifting leading to the production of the third possible reading phase.

After insertion of the DNA-HVB in each of these three vectors, it is understood that one of these three vectors will be in any event adapted to be translated correctly by the suitable bacteria hosts, with consequently the production of a hybrid protein containing that which corresponds to DNA-HVB.

Other characteristics of the invention will appear also in the course of the description which follows of an example of cloning of the genome of the B hepatitis virus in the λgtWES.λB phage.

Reference will be made to the drawings, in which:

FIGS. 7B–7I illustrate diagrammatically the steps in the manufacture of a vector of the plasmid type incorporating a fragment of HBV DNA.

Figure 8D:
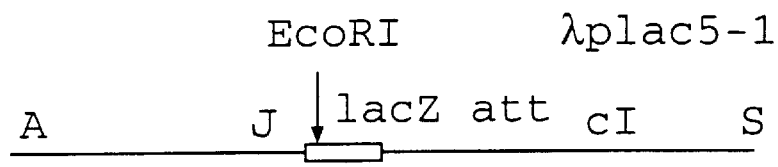
Figure 8E:
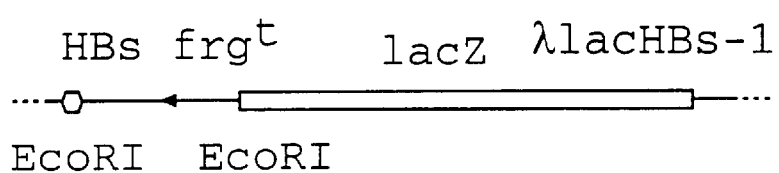
Figure 8F:
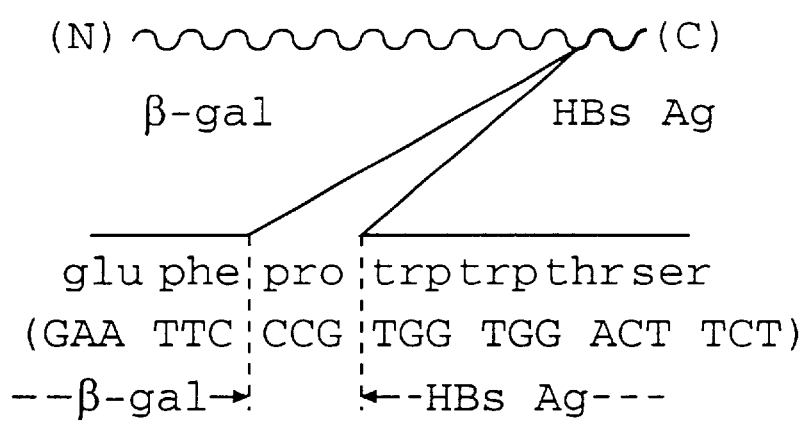

FIGS. 8A–8C show the two mutually complementary strands of DNA sequence. FIG. 8D is a diagramatic chart of a vector. FIG. 8E is a diagramatic chart of FIG. 8D showing a modification included into its gene Z. FIG. 8F shows a diagramatic structure of the hybrid polypeptide obtained as a results of the expression of the modified vector of FIG. 8E.

FIGS. 9A–9C show the nucleotide structure of the gene S and the polypeptide chain resulting from the translation of the gene.

FIGS. 10A and 10B show the two mutually complementary strands of DNA sequence.

FIG. 11 shows the peptidic sequence coded by nucleotide sequence.

FIG. 12 shows a nucleotide encoding a peptide sequence according to the invention.

Figure 1:
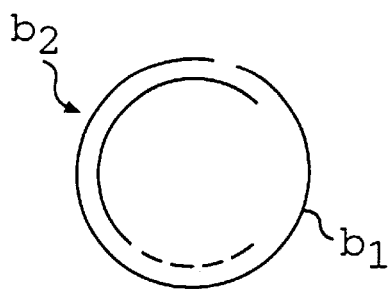
FIG. 1 is the diagrammatic representation of a natural DNA-HVB, already referred to in the preamble.

FIG. 1 shows diagrammatically a viral DNA, such as obtained from a Dane particle. It comprises a single strand region $b_1$ and a double strand region $b_2$.

Figure 2:
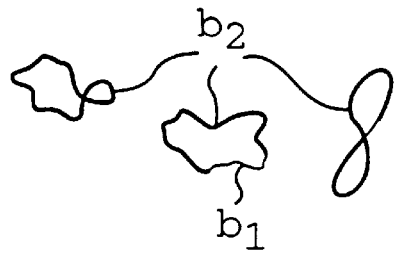
FIG. 2 is a diagram derived from a photograph of three DNA-HVB molecules taken by an electron microscope, of which two are partly monocatenary.

These regions $b_1$ and $b_2$ are marked in the diagrams of FIG. 2 by thin and thicker lines, respectively.

1.) Purification and Repair of the DNA of the B Hepatitis Virus (DNA-HVB)

400 milliliters of serum rich in Dane particles, distributed in 12 fractions of 25 milliliters, were deposited on saccharose gradients 10–30% (weight/volume) in 10 mM Tris-HCl buffer at pH 8, 10 mM EDTA, 1 M NaCl (TEN Buffer). The centrifugation was effected in a BECKMAN SW27 rotor at 5° C. at 25,000 rpm for 15 hours. Each deposit (containing the Dane particles), was taken up in 0.5 ml of TEN buffer and treated by ultrasound. The suspension (6 ml) was deposited on two saccharose gradients 10–30% and centrifuged in a BECKMAN SW50-1 rotor at 5° C. at 50,000 rpm for 2 hours. The deposits were taken up again in 1 ml of TEN buffer, containing CsCl so as to obtain a density of 1.23 g/ml. This suspension was centrifuged in a BECKMAN SW60 rotor at 20° C. at 55,000 rpm for 15 hours. The gradient was collected in a fraction of 50 µl. The polymerase activity was detected by measurement of the incorporation of ATP and TTP $\alpha^{32}P$ in an acid precipitatable material described by W. S. ROBINSON (Ann. Rev. Microbiol., 31, 1977) or by T. A. LANDERS et Coll. (J. Virol. 23, 1977, p. 368–376).

The fractions in which the incorporation of $^{32}P$ was at a maximum had a density of 1.23 g/ml. These fractions (containing the Dane particles) were labelled under the same conditions by a mixture of ATP and TTP $\alpha^{32}$ P, having a specific activity 10 times less (this to avoid degradation of the DNA). These fractions were incubated for 1 hour at 37° C. in the presence of pronase (10 mg/ml) and of sodium dodecyl sulfate (1%), and then the DNA was extracted by two successive treatments with a phenol-chloroform mixture (1 vol/1 vol). The DNA was precipitated by the addition of 2 volumes of ethanol at −20° C., then dissolved in 100 αl of TEN buffer. The concentration of DNA was determined by taking into account the specific activity of the triphosphate precursors, the proportion of single stranded DNA, which is on the average 30%, and the fact that the endogenous polymerase DNA repairs about one half of the single stranded region. The determination of the DNA concentration was confirmed by electrophoretic analysis on agarose gel. The 100 µl (corresponding to 400 ml of plasma) contained about 1 µg of DNA. The examination under the electron microscope showed that the preparation contained in fact circular DNA of expected length and in which most of the molecules posses a single strand region of variable length. The proportion of linear molecules of the same length as the circular DNA was about 10%.

2.) In Vitro Manufacture of Recombinants Between DNA-HVB and Two Fragments of the λqtWES. B.

30 ng of DNA-HVB were mixed with 500 ng of vector fragment (which corresponds to a molecular ratio close to 1) and were treated by EcoRI endonuclease. Hydrolysis of the DNA-HVB in the presence of the DNA vector enable the dilution by the latter of possible contamination nuclease activities. After hydrolysis, the fragments were separated by electrophoresis on a polyacrylamide gel (gel gradient having concentrations of acrylamide varying from 2.5 to 7.5%). The factions obtained were concentrated by chromatography on hydroxylapatite as described previously (TIOLLAIS et al. FEBS. LETTERS, 48 (1974) 96–100). The concentrates obtained were dialysed against a 50 mM Tris-HCl solution at pH 7.5, containing 60 mM of sodium chloride.

Ligation of the fragments then followed by the technique described by MURRAY & MURRAY, NATURE, 251 (1974), 474–481, except for the following modifications. In particular, the DNA solutions contained 30 ng/µl of DNA (the molar ratio between the vector fragments and the fragments to be inserted being comprised between 2 and 6) within a Tris-HCl buffer, at pH 7.5, and 60 mM of sodium chloride. These solutions were heated for 5 minutes at 50° C., to dissociate the cohesive ends. The components identified hereafter were then introduced into the mixture to obtain final concentrations of, respectively, 10 nM $MgCl_2$, 10 nM of dithiothreitol, 0.1 mM ATP, and 50 µg per milliliter of bovine serum albumin. A ligase polynucleotide T4 was then added (notably that produced by MILES LABORATORIES, LTD) and the medium was incubated at 0° C. for 20 hours.

3.) Cloning in the Strain C600 recBC rk⁻mk⁻.

The transfection of the strain identified above was carried out according to the method described by CAMERON & Coll., Proc. Natl. Acad. Sci. U.S.A., 72 (1975) 3416–3420. The strain was then spread over lactose MacConkey medium. Eight independent clones were amplified in the strain DP50 Sup. F. The DNA was then cleaved by the EcoRI enzyme and the fragments were analysed by electrophoresis on agarose gel. In all cases, the latter revealed the presence of an EcoRI fragment which migrated as the slowest fraction. The latter was formed by DNA-HVB, and its size could be estimated at about 3200 pairs of bases.

4.) Identification Among the Cloned DNAs of the Fragment Corresponding to DNA-HVB The DNA of the recombinant bacteriophage (λHVB 1) was hybridized with the initial DNA-HVB in the ratio of three molecules of DNA-HVB per one molecule of DNA λHVB 1.

Figure 3:
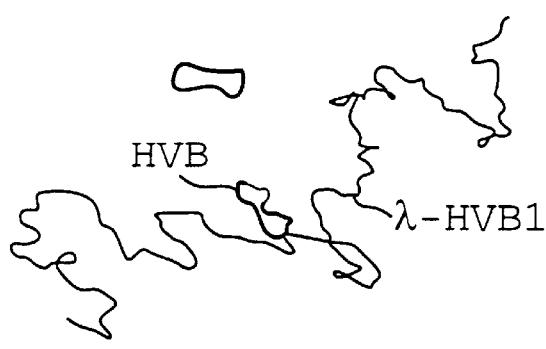
FIGS. 3 to 6 are reproductions drawn from photographs taken under the electron microscope of heteroduplexes between recombinants of DNA of λ phage and that of DNA of viral hepatitis, on the one hand, and of DNA derived directly from Dane particles, on the other hand.
Figure 4:
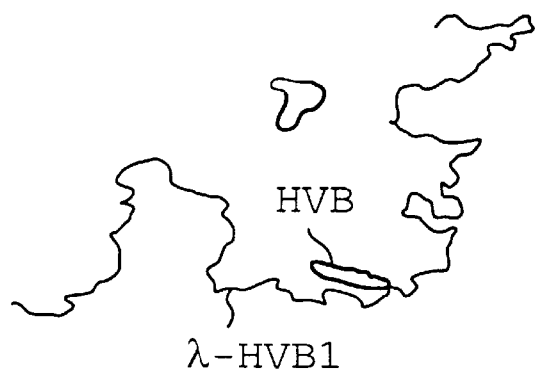
Figure 5:
Figure 6:
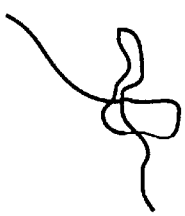

The heteroduplex molecules observed contained a bicatenary loop of a size equal to that of the bicatenary DNA-HVB and situated at the expected position in the genome of the bacteriophage. Two types of loops were observed; either an entirely bicatenary loop or a loop carrying a monocatenary region situated in the central region of the inserted EcoRI fragment (FIGS. 3 and 4). When the two strands of the vector were paired, two loops were observed (FIGS. 5 and 6).

Different arguments show that the cloned DNA is indeed DNA-HVB. After digestion of the DNA of the hybrid lambda bacteriophage (HVB-1) by the EcoRI endonuclease, electrophoretic analysis shows the presence of a fragment having the length of DNA-HVB. In the same way, the heteroduplex loops observed after hybridization have the same length. The existence of bicatenary loops carried by the monocatenary DNA proved that the DNA that was inserted was circular before the cleavage by the EcoRI enzyme. The presence of two types of loops (entirely and partly bicatenary) proves that the original DNA was formed of two paired chains and of equal sizes. The characteristics fit well with those of the B hepatitis genome.

The abundance of heteroduplex molecules possessing the expected structure is important. This establishes that the fragment cloned was not a DNA contaminant, since in the preparation of DNA-HVB the electron microscope enables a less than 1% contamination to be detected.

The DNA clone represents apparently the whole of the genome of Dane particles. In fact, the structure of the heteroduplex molecules indicated that the most fragile part of the DNA-HVB, namely the monocatenary region, has been indeed incorporated. In addition, the length of the cloned DNA shows that, if the latter were shorter than the DNA of the Dane particles, the difference in length would be less than the errors in measurement, namely about 150 pairs of bases. All of the foregoing results confirm also the existence of a single EcoRI restriction site in the DNA-HVB.

The thus-cloned DNA-HVB can be labelled in vitro, notably with a radioactive sotope $^{32}P$. It is advantageously applied as a probe to detect the presence of Dane particles, for example in human serum. It is possible to this effect to resort to any conventional DNA-DNA hybridization technique.

The invention also concerns a method for the production of a hybrid protein containing a protein fragment having vaccinating activity against hepatitis B, which comprises introducing the above-defined vector in bacteria, causing the latter to translate at least the part of said vector which contains the DNA corresponding to that of hepatitis B, and recovering said hybrid protein.

As is itself evident and as also emerges from the foregoing, the invention is in no way limited to those of the embodiments and applications which have been more especially contemplated; it encompasses on the contrary all modifications, notably those in which recourse is had for the cloning according to the invention to other genetic modifications of the DNA of B hepatitis virus.

It will be recalled that PETERSON and co-workers have reported, notably in the articles of which the references are recalled above, that the proximal sequence (first N-terminal amino acid) of the 15 first amino acids is in principle as follows:

Met Glu Asn Ile Thr Ser Gly Phe Leu Gly Pro
Leu Leu Val Ser and that the terminal sequence of these same polypeptides (last C-terminal amino acid) was the following:

Val Tyr Ile.

Figure 7A:
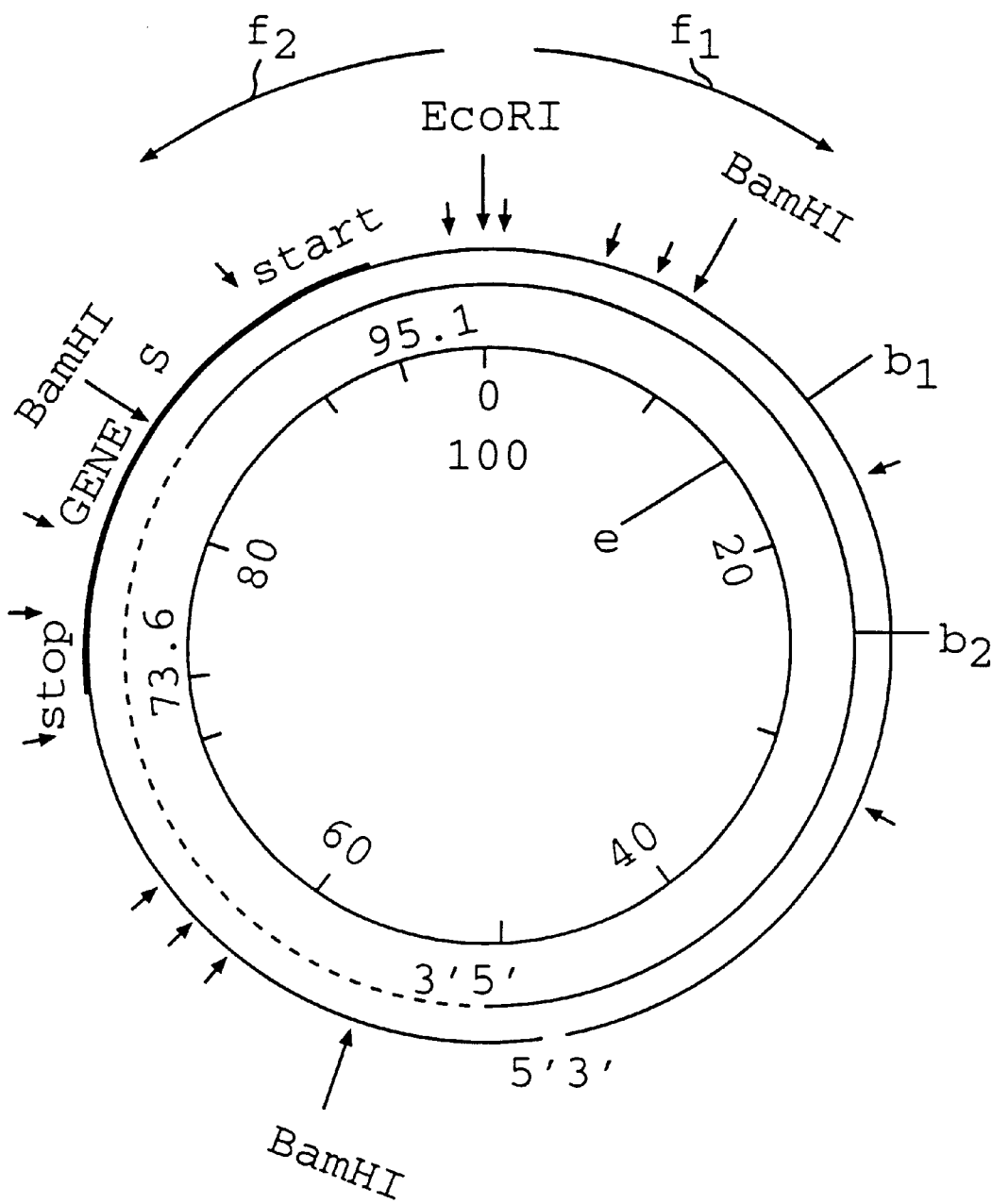
FIG. 7A is a diagramatic chart of the genome of the Dane particle.

FIG. 7A is a diagrammatic chart of the genome of the Dane particle. The latter includes two strands $b_1$ and $b_2$; the shortest of them ($b_2$) being normally devoid of the portion represented by an interrupted line in the drawing.

It is known that this DNA only includes a single EcoRI site.

The arrow $f_1$ gives the direction of numbering of the nucleotides from which the longest strand $b_1$ is composed, and the arrow $f_2$ gives the direction of transcription of the DNA of the virus, notably by the cellular mechanism of the cells invaded by the virus of hepatitis B, as regards the expression of the gene S.

The EcoRI site can hence be numbered 0 or, as has now been determined more exactly for that of the hepatitis B virus belonging to the serotype ayw, 3,182.

The inner circle e in continuous line gives the scale in % of the length of the DNA and permits the positions of certain of its parts to be specified.

The numbers 3', 5' and 5', 3' at the lower part of the chart are aimed at the terminal ends bearing the same numbers in conventional representation of the ends of the nucleic acid chains.

According to the invention, it has been shown that the "gene S" constituted essentially the fragment of the longest strand $b_1$ situated between the positions 73.6 and 95.1 of the diagrammatic map of FIG. 7. The abbreviations "Start" and "Stop" represent the initiation and stopping points of the transcription of the "gene S".

FIGS. 8A, 8B, 8C are representative of the terminal portion of the above-said genome, comprised notably between the positions 60.4 and 100 (in % length of DNA). Each of the letters shown in FIGS. 8A–8C correspond conventionally to one of the 4 basic nucleotides of DNA:

A : Adenine
G : Guanine
T : Thymine
C : Cytosine.

The lower lines, in each pair of lines from which FIGS. 8A, 8B, and 8C are constituted, correspond to the nucleic acid corresponding to the nucleotide chain $b_2$.

The analytical technique used to establish the more detailed map represented by FIGS. 8A, 8B, and 8C, will be briefly recalled below.

The characterization of the nucleotide of the "gene S", such as proposed within the scope of the present invention, and of which the proximal ends p "S" and terminal ends t "S" are indicated in FIGS. 8A, 8B, and 8C, results from the observation that:

the first 14 triplets (in the direction of reading $f_2$) from the nucleotide numbered 3,030 with respect to the EcoRI terminal end, are respectively capable of coding the 14 first amino acids of the proximal sequence of the 15 first amino acids of the above-said polypeptides, the 4 last triplets GTA TAC ATT TAA read in the complementary chain $b_2$ to the transcribed chain $b_1$ correspond respectively to the 3 terminal amino acids of the abovesaid polypeptides and to a stop codon;

this sequence of neceleotides (678 nucleotides) does not comprise any stop codon, at least when the reading frame is adopted implying that the first triplet "read" on the DNA by the cellular mechanism is AUG, (corresponding to a strand complementary to ATG);

the complete translation of the genetic information commencing with the initial codon ATG leads to a theoretical polypeptide of 226 amino acids, having a molecular weight of 25,422 daltons.

The nucleotide structure of the "gene S" as well as the polypeptide chain resulting from the translation of the "gene S" are shown in FIGS. 9A, 9B, and 9C.

These values are quite in accordance with the analytical data which result from the electrophoretic mobility of the polypeptide I on polyacrylamide gels which have already been described by the preceding authors (references 9–12 according to the bibliography at the end of the description of the present patent application).

The difference observed at the level of the 15th amino acid of the proximal peptide sequence of the polypeptide I : leucine according to the charts of FIGS. 8A, 8B, and 8C, and 9A, 9B, and 9C mentioned above, and not serine according to the observation of the above-said authors, may perhaps be attributed to the fact that these authors have worked with a genetic variant different from that which is the subject of the present study. It will be noted that the difference can besides be attributed to the substitution of a single nucleotide in the "TTA" triplet concerned in the particular "gene S" shown in the maps of FIGS. 8A, 8B, and 8C and 9A, 9B, and 9C, instead of "TCA", one of the triplets capable of being translated into serine.

The invention hence relates more particularly to the fragments of the nucleic acid, which can be excised from the DNA of the Dane particle, these fragments being more particularly characterized in that they contain the portion of the "gene S" capable of coding the portion of the protein of the envelope of the virus, which is responsible for the immunological properties of the hepatitus B virus.

Accordingly, the invention relates therefore to a nucleic acid comprising at the most of the order of 1,000–1,100 nucleotides, more particularly characterized in that it is adapted to induce in vivo the production of active antibodies with respect to the hepatitis B virus, this peptide sequence containing essentially the structure shown in FIGS. 9A, 9B, and 9C, or any peptide sequence having equivalent immunogenic properties.

The invention also relates to a vector for the expression of said nucleotide sequence in a microorganism or in eucaryotic cells on condition that the genetic fusion has been carried out by preserving the reading phase of the "gene S".

The nucleotide sequences used according to the invention have with respect to one another a variability leading, on their expression, to the formation of determinants varying according to the sub-type of the hepatitis B virus (sub-types d, w, y, r of group a).

For one of the peptide sequences shown in FIGS. 9A, 9B, and 9C, it will be observed that the first amino acid of the above-said sequence: methionine, is N-terminal and that the amino acid of the opposite end: isoleucine, is C-terminal.

The invention also relates, more particularly, to the nucleotide sequence represented in FIGS. 10A and 10B, coding the peptide sequence such as results from FIG. 11 or similar peptide sequence endowed with equivalent immunogenic properties.

It is self-evident that by "eqivalent peptide sequence", mentioned above, must be understood any peptide sequence in which certain parts may not be strictly identical with corresponding parts of the peptide sequence shown in FIGS. 9A, 9B, and 9C and 11, these variations being attibutable to local mutations not affecting the general immunogenic character of the protein or with structural modifications owing to the different serotypes in which proteins of the type concerned can occur (notably serotypes adw, adr, and ayr).

The invention relates more particularly to the nucleotide sequence containing the peptide sequence as shown in FIG. 12 or any similar peptide sequence endowed with equivalent immunogenic properties.

The invention relates more particularly again to the following peptide sequences:

Alanine-Glutamine-Glycine-Threonine-Serine

Threonine-Alanine-Glutamine-Glycine-Threonine-Serine

Threonine-Threonine-Alanine-Glutamine-Glycine-Threonine-Serine

In the first above-indicated peptide the alanine end is N-terminal and the serine end is C-terminal.

In the second or third above-mentioned peptides, the threonine end is N-terminal and the serine end is C-terminal.

By way of example, it is possible notably to prepare the pentapeptide starting from the C-terminal serine to which threonine is fastened by the Castro method described in Tetrahedron Letters, 1975, No. 14, page 1219–1222. Then the amino acids glycine, glutamine, alanine are added by the so-called repeated mixed anhydride method (rema method) described by Beierman in Chemistry and Biology of Peptides, Ed. J. Meienhofer, Ann Arbor Science Publ., Ann. Arb. Mich. 341 (1972).

The invention also relates to the products resulting from the fixing of the pentapeptide on to a larger carrier molecule, notably of the polypeptide or protein type, the composition containing this pentapeptide in fixing products, notably in association with a pharmaceutically acceptable vehicle, and more particularly vaccines against hepatitis B. These pharmaceutical vehicles are suited, conventionally, to the selected method of administration, notably orally, parenterally, rectally, or by nebulization onto the mucous membranes, notably the nasal membranes.

The hexapeptide and the polypeptide with 7 amino acids can be synthesized by conventional peptide synthesis techniques.

These peptides are, according to the present invention, believed to be the antigen site of the polypeptides of larger size considered above and responsible for the vaccinating power of the viral envelope (Journal of Biol. Stand. 1976, 4, 295–304, RAO and VYAS "Biochemical Characterization of Hepatitis B Surface Antigen in Relation to Serologic Activity").

Again the invention relates also to the DNA fragments capable of coding the production of such pentapeptide, hexapeptide, and polypeptide with 7 amino acids. It relates to:

for the pentapeptide, notably the polynucleotide of the formula:

```
5' CCT CAA GGA ACC TCT 3'
3' GGA GTT CCT TGG AGA 5'
``` for the hexapeptide, notably of the polynucleotide of the formula:

```
5' ACT GCT CAA GGA ACC TCT 3'
3' TGA CGA GTT CCT TGG AGA 5'
``` for the polypetide with 7 amino acids the polynucleotide of the formula:

```
5' ACT ACT GCT CAA GGA ACC TCT 3'
3' TGA TGA CGA GTT CCT TGG AGA 5'
``` or in each of the three cases, of the complementary polynucleotide relating to the three preceding respective polynucleotides or again any polynucleotide in which each of the triplets can be replaced by any similar triplet capable of coding the production of the same amino acid.

The nucleic acid according to the invention can also be characterized in that it comprises at least one of the two mutually complementary strands of a DNA sequence, such as shown in FIGS. 10A and 10B (in which are also shown the numbers corresponding to the positions of the first nucleotides of each of the successive fragments of 10 nucleotides shown with respect to the EcoRI position not shown in the Figure: It is self-evident that these numbers do not come into consideration at the level of characterization of the nucleotide sequence of the type concerned). This DNA fragment is bounded by two sites.

It will be appreciated that this nucleotide sequence corresponds to the genetic information whose translation leads to the peptide sequence shown in FIG. 11.

The invention relates naturally to equivalent nucleotide sequences with a single strand or double strand, of which notably the strand having the structure which arises from the succession of lower lines of FIGS. 10A and 10B, the corresponding double strand DNA, or the corresponding messenger RNA's, notably that shown by the complementary chains of nucleotides constituted by the lower lines of the pairs of lines of FIGS. 10A and 10B (direction of the arrow $f_2$).

In the same way there come within the field of the invention the nucleotide chains which are differentiated from the preceding ones by certain triplets or small sequences of triplets, to the extent that these nucleotide sequences remain adapted to code a polypeptide preserving the characteristic immunogenic activities of the virus of viral hepatitis B. In general, it relates to nucleotide chains which, possibly, after denaturation of the double strand DNA to produce the corresponding single strand nucleic acids, remain capable of hybridizing over at least about 90% of their length with one of the DNA strands of FIGS. 10A and 10B.

Preferred nucleic acids according to the invention are also those which can be excised from DNA of viral hepatitis and which, when they are double strand, are characterized by the existence at one of their ends of an HincII, HhaI, AvaI or EcoRI extremity and at their other end by an AvaIII, HincII or HhaI extremity.

The positions of these various extremities with respect to the EcoRI site are shown diagrammatically in FIGS. 8A, 8B, and 8C.

The nucleic acid according to the invention is intended for incorporation in a vector enabling its expression in a bacteria and in eucaryotic cells, notably for the production of a protein or of a peptide capable of inducing in the organism of a living host the production of active antibodies against the virus of viral hepatitis B. The protein or peptide resulting from the translation of the nucleotide sequence according to the invention can be used as a vaccinating agent or as an agent serving for diagnosis.

The nucleic acid according to the invention can also be used as a probe to track down the presence or not in blood samples or test serum, of the Dane particle, of the HBs antigen, or of fragments of the latter, etc. (by the conventional DNA-DNA hybridization technique).

Other characteristics of the invention will result also from the brief description which follows of the techniques of analysis of identification and of production of DNA fragments according to the invention. Reference will naturally be made to the drawings whose Figures have already been taken into consideration in the foregoing. The Figures or numbers between parentheses correspond to the references of the bibliography appended to the present description.

The invention relates also to particular vectors enabling the expression of the above-described nucleotide sequences, notably in the form of a hybrid protein in which a protein fragment having the immunological character of HBsAg added to a carrier molecule conferring on the whole immunogenic or immunoreactive properties, capable of inducing the production of protective antibodies with respect to viral infection in the organism of the host into which this protein has previously been introduced.

In particular, the invention relates to a vector-phage or plasmid, containing at least a part of the lactose operon, more particularly the promoter and the Z gene of this operon, this vector being characterized in that it is modified for the insertion, in phase, in a suitable site of the Z gene, such as the EcoRI site of any one of the DNA fragments of the principal patent, notably those containing the largest part of the "S gene". It relates also to those of these modified vectors, in which a part at least of the coding DNA fragment for the largest part of the β-galactosidase would be replaced by a DNA fragment adapted to code for any other non-immunogenic carrier molecule, or of which the possible immunological properties, if the latter exist, do not interfere with those of the peptide part having the immunological properties of HBsAg, for example essentially that which extends in the direction of reading from its HhaI site.

The invention relates also more particularly to a hybrid protein characterized in that it contains polypeptide sequence having the specific immunological properties of HBsAg, contiguous with a polypeptide sequence constituted for the most part of β-galactosidase, which plays the role of carrier-protein.

The invention does not extend only to this particular hybrid molecule, whose essential role is to constitute a model of a protein constructed according to the techniques of genetic engineering and endowed with immunogenic and immunoreactive properties characteristic of the HBsAg antigen, but also to any other hybrid protein in which all or part of the β-galactosidase may be replaced by any other non-immunogen carrier molecule, or of which the possible immunological properties, if the latter exist, do not interfere with those of the peptide part having the immunological properties of HBsAg.

Other characteristics of the invention will appear also in the course of the description of preferred examples, in combination with the drawings in which:

HBV DNA,

FIGS. 8D to 8F illustrate diagrammatically the initial structures of the final vector used (FIG. 8D) of the modified vector obtained (FIG. 8E) and that of the hybrid protein resulting from the expression of this modified vector into *E. coli*. (FIG. 8F).

A. NUCLEOTIDE SEQUENCES

Products and Methods Used

The Enzymes and Chemical Substances Used

The restriction enzymes used: BamHI, HhaI, HincII, HaeIII, XbaI, MboI, HinfI, HpaII, XhoI, are those manufactured by BIOLABS. DNA-polymerase I of BOEHRINGER was used. The bacterial alkaline phosphatase and the polynucleotide-kinase were supplied by P. L. BIOCHEMICALS. The chemical agents were the following:

Dimethyl sulfate (ALDRICH),

Hydrazine (EASTMAN KODAK),

Acrylamide and bis-acrylamide (twice crystallized—SERVA),

Dideoxy nucleotide triphosphates and deoxy-nucleotide triphosphates (P. L. BIOCHEMICALS), Piperidine (MERCK) redistilled in vacuo Preparation of DNA HBV The whole HBV genome (sub-type ayw) was cloned in *E. coli* by bringing into play the single EcoRI restriction site of λgt. WES. λB vector (14). The cloned DNA is called below "Eco HBV DNA".

The recombinant bacteriophage was grown in a Petri dish on agar and the desired DNA was extracted in manner known in itself. After digestion of the DNA by the EcoRI restriction enzyme, the Eco HBV DNA sequence was purified by ultracentrifugation, in a sucrose gradient, according to the technique described in the bibliographical references (16, 17).

Preparation of 5' $^{32}$P Labelled DNA Fragments 10 to 20 picomoles of Eco HBV DNA were completely hydrolyzed by the various restriction enzymes, under the conditions recommended by the manufacturer. The DNA fragments were dephosphorylated by alkaline phosphatase, the latter having then been inactivated by alkaline treatment. The DNA was then precipitated with ethanol by the technique described in the article (18). After redissolving in a buffer based on spermidine, the DNA's were labelled at their 5' ends with an ATP {$\lambda^{32}$P (3,000 Ci/mM manufactured by NEW ENGLAND NUCLEAR)} and with polynucleotide kinase (according to the technique indicated in the article 19).

The DNA restriction fragments were separated by electrophoresis on polyacrylamide gel, then eluted. The labelled ends were the subject of segregations by electrophoresis on polyacrylamide gel in manner known in itself, after restriction with another enzyme or by denaturation of the DNA fragments of the type concerned.

Determination of the Structure of the Nucleotide Sequences of DNA

The primary structure of the double strand or single strand DNA fragments was determined essentially according to the technique described by MAXAM and GILBERT (19). Recourse was also had to the method of terminal chain inibitors described by SANGER et al. (20) and adapted by MAAT and SMITH (21), as regards the double strand fragments labelled at one of their 5' ends.

The chemical and enzymatic reaction products were analyzed by electrophoresis in gels of acrylamide in sequence at 8, 16, or 25% of 1 mm thickness.

Analytical Techniques and Results

In order to determine whether the HBV genome is capable of coding the polypeptides I and II, all the HaeIII fragments (HaeIII restriction sites of the HBV genome shown in FIG. 7A by small arrows) were labelled at their 5' ends. Substantial portions of their primary structures were determined by the method of MAXAM and GILBERT. The nucleotide sequences capable of coding the proximal and terminal amino acid sequences of the polypeptides I and II were localized in the HaeIII E and HaeIIIFF fragments, previously localized on the restriction map of the HBV genome, according to the technique described in the reference (17). It is these nucleotide sequences which have been considered as consisting of the ends of the "gene S" occupying themselves the positions 73.6 and 95.1 with respect to the EcoRI restriction site (FIG. 7A) for the reasons already indicated.

The nucleotide sequence between these two positions has been analyzed by resorting to known chemical techniques, notably by the chemical degradation method with hydrazine dimethyl sulfate and the method of chain termination. Recourse was had, among the various chemical reactions proposed by MAXMAM and GILBERT, to a partial depurination by formic acid and with cleavage by piperidine, methods which give equal intensity bands on autoradiograms for the fragments terminated by guanine and an adenine. Reactions with hydrazine followed by cleavage with piperidine were also used to obtain bands of equal intensity, for the cytosine and thymidine nucleotides: electrophoretic fractionation of the products of these two reactions gives for all the bases a spot in one or the other of the gel columns used. This procedure facilitates the reading of the autoradiogram of the gel. The reaction with hydrazine in the presence of sodium chloride specific for cytosine enables this nucleotide to be distinguished from thymidine and the reaction with dimethyl sulfate followed by clevage by piperidine, specific for guanine, enables the latter nucleotide to be distinguished from adenine.

In order to ensure the greatest possible degree of accuracy, distinct sequences of nucleotides forming different mutually straddling fragments were produced by hydrolysis of Eco HBV DNA by various restriction enzymes:

BamHI, HinfI, HpaII, HaeIII, and HincII.

In this way the analysis of each of the restriction sites used as starting points of the first fragments studied was confirmed by analysis of the separate fragments in which the restriction sites of the first fragments are comprised between the new ends of these separate fragments.

The "gene S" shown in FIGS. 9A, 9B, and 9C, which commence by the initiation codon ATG, comprises 227 triplets, including a stop codon TAA. The three codons corresponding to the 3 amino acids of the terminal carboxy end of the corresponding polypeptide are situated in the same reading frame, immediately before the stop codon TAA. One of the two other reading frames (respectively offset to the preceding one by 1 and 2 nucleotides) is also devoid of a stop condon, but codes quite a different protein from the polypeptides I and II mentioned above. The third reading frame comprises 10 stop codons (5 TAG, 4TGA, 1TAA). On the other DNA strand, the three reading frames are respectively closed by 11, 11, and 6 stop codons distributed along the DNA sequence.

As has already been indicated above, the complete translation of the genetic information starting by the initiation codon ATC leads to a theoretical polypeptide of 226 aminoacids corresponding to a molecular weight of 25,422 daltons.

It is interesting to stress that the nucleotide sequence corresponding to the "gene S" should normally be read entirely in the course of translation.

Equally to be regarded as part of the invention are the nucleotide chains of the above-described "gene S" type, which comprises small additional sequences which can contain up to one hundred nucleotides or which on the contrary may be devoid thereof, without however the corresponding genetic information being altered (22, 23).

The various fragments of the invention which have been defined above may be obtained from the so-called Eco HBV DNA DNA sequence, by resorting to the corresponding restriction enzymes and to the known fractionation techniques of DNA fragments, notably on a polyacrylamide gel and applying their migrations over distances which are a function of their molecular weights. Thus, it is possible, for example, to obtain the fragment of which one of the ends is bounded by an EcoRI site and the other by an AvaIII site by operating an Eco HBV DNA restriction by the AvaIII enzyme, the desired fragment consisting of the smallest fragment obtained (a single AvaIII site in Eco HBV DNA).

The fragment bounded by the opposite ends EcoRI and HhaI is obtained by hydrolysis of Eco HBV DNA by EcoRI first, then by partial hydrolysis by the restriction enzyme HhaI. Among the restriction products was then recovered that which contains the AvaII site.

These restriction techniques have obviously only been proposed by way of example, it being well understood that the specialist is himself able to determine the order of treatment with restriction enzymes to isolate, starting notably with Eco HBV DNA, the fragments having useful restriction ends.

Insofar as it may be useful, it is recalled that these restriction operations can be carried out in a 10 mM Tris buffer at pH 7.8; 6 mM $MgCl_2$; 6 mM$\beta$-mercaptoethanol, the same medium containing in addition preferably 50 mM of NaCl when EcoRI is used.

As has already been said, the invention relates to the use of the DNA fragments described as a probe enabling diagnosis of the presence in a serum of Dane particles or particles derived from the preceding one, bearing a DNA capable of coding an immunogenic protein characteristic of hepatitis B.

The DNA according to the invention can also be incorporated in a vector enabling, on condition that the incorporation has been carried out in phase, the expression of this DNA into a bacterium or other microorganism, or into eucaryotic cells.

B.—VECTORS CONTAINING A NUCLEOTIDE SEQUENCE OF HBs ANTIGEN

Construction of a $\lambda$lac HBs-1 Recombinant Bacteriophage

The products at the level of the different stages of this construction are indicated in FIGS. 7B and 7I. They are also indicated by the numbers 1$a$ to 1$h$.

In FIG. 7B are indicated the positions of the "gene S" and of certain restriction enzyme sites.

After treatment of DNA+HBV with HhaI restriction enzyme, a DNA fragment (1$b$) was separated containing 1,084 pairs of bases, and more particularly the whole of the "gene S" by electrophoresis on agarose gel and electroelution (FIG. 7C). There was prepared from this sub-fragment, treated previously by endonuclease SI, a sub-fragment (1c) (FIG. 7D), resulting from the elongation of the sub-fragment (1b) at its ends, by DNA elements named "EcoRI linkers" of the formula:

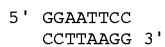

The fragment obtained was, after formation of the EcoRI cohesive ends, cloned in the plasmid pBR322.

The plasmid obtained, named below pBRHBs (FIG. 7E), only contains a single restriction site XbaI located close to the head of the "gene S".

By digestion of the pBRHBs recombinant plasmid with a mixture of EcoRI and XbaI enzymes, a DNA fragment comprising approximately 980 pairs of bases and including the major part of the "gene S" (FIG. 7D) was produced. This fragment was separated and purified by electrophoresis on agarose gel. The fragment obtained was again treated with SI endonuclease, then again provided with EcoRI ends by means of the above-said "EcoRI linkers", then subjected to treatment with EcoRI endonuclease to reform the corresponding cohesive ends. The fragment of FIG. 7F, which comprises about 980 pairs of bases, is then inserted by in vitro fusion into the EcoRI site of the plasmid pBR322, to form the plasmid pXbaHBs (FIG. 7G). This plasmid was cloned in the usual manner like the plasmid pBR322.

Several clones were obtained.

There were extracted and purified, after treatment with EcoRI in DNA's of three of these clones, pXbaHBs-1, pXbaHBs-2, pXbaHBs-3 (FIG. 7H), the fragments called below "HBs fragments" (FIG. 7I).

The nucleotide sequences of the ends of the above-said fragments (normally obtained inside the "gene S") were determined by resorting to the procedure described by MAXAM and GILBERT (Proc. Nat. Acad. Sci. USA 74, 560–564 (1977)). These determinations have shown that the sequences of the nucleotides of the terminal ends, corresponding to the "gene S" were not identical in the three clones (FIG. 7H); the differences are apparently due to heterogeneities produced in the course of digestion with the S1 endonuclease.

The two fragments coming from the pXbaHBs-1 and pXbaHBs-2 were inserted by fusion in vitro into the bacteriophage genome λplac 5-1 (21), which had only a single EcoRI site situated close to the end of the lac Z gene. Due to the fact of the reading frame of the lac Z gene, such as can be produced from the amino acid sequence of β-galactosidase (23), it is observed—and experiment confirms it—that the insertion of the HBs fragment of pXbaHBs-1 into the EcoRI site of the lac Z gene of λplac 5-1 must lead to the preservation of the adequate reading phase of the "gene S". On the contrary, the insertion of the HBs fragment of pXbaHBs-2 should be revealed as not capable of being inserted into the preceding vector with preservation of the suitable reading frame. It has, nontheless, been used as a control in later experiments.

These operations were carried out by resorting to known techniques. In particular, the "HBs fragments" of pXbaHBs-1, pXbaHBs-2 were inserted by means of a ligase into the DNA of λplac 5-1 which had previously been cleaved by EcoRI. The mixtures of DNA fragments obtained where then used to transfect the strain C600RecBC rk⁻mk⁻ of E. coli. The bacteriophage clones become lac⁻ due to the fact of the insertion of the HBs fragments into the EcoRI sites of the lac Z gene and were amplified and purified by the method described in (21).

The DNA's of the different bacteriophages were extracted and the orientations of the DNA fragments inserted were determined by electrophoretic analysis of their BamHI restriction fragments. It was thus possible to determine that two phages called lacHBs-1 and lacHBs-2 corresponding to the pXbaHBs-1 and pXbaHBs-2 plasmid contained a correctly oriented HBs fragment.

FIG. 8D is a diagrammatic chart of the plac 5-1 vector before its modification by the HBs-1 fragment, coming from the pXbaHBs-1.

FIG. 8E is a diagrammatic chart of a portion in this same vector showing the modification introduced into its gene Z by insertion into its EcoRI site of the above-said HBs-1 fragment.

FIG. 8F shows diagrammatically the structures of the hybrid polypeptide obtained as a result of the expression of the modified vector of FIG. 8E.

The expression was achieved by a transfection of a strain of E. coli bacteria, notably of HfrΔlacX74.

The strains of E. coli, notably a strain of E. coli Hfr lac X74 were converted by plac 5-1 and λlacHBs-1 and λlac HBs-2, respectively. After cultivation, the cells were lysed and the lysates obtained analysed by electrophoresis on SDS polyacrylamide gel (24), and the proteins were detected by dyeing with coomassie blue. The presence of a stronger band among the expression products of λplac 5-1 was detected at the level of the position corresponding, for a control, with that of β-galactosidase (molecular weight of 116, 248) and of a separate band among the expression products of λlacHBs-2) corresponding to a novel protein having a molecular weight of the order of lac HBs-2)135,000–141,000.

The proteins synthesized by the bacteria transfected both by λlacHBs-1 and by λplac 5-1 were labelled with (³⁵S) methionine. The contacting of these proteins with an anti-HBsAg serum and the production of an autoradiogram of the SDS polyacrylamide gel reveal the presence among the expression products of only λlacHBs-1 of a band to which there does not correspond an equivalent band among the expression products of the other vectors. This band disappeared specifically when immunoprecipitation was carried out in the presence of unlabelled HBsAg. There was also observed the same band among the λlacHBs-1 expression products, when immuno-precipitation was carried out with an antiserum with respect to β-galactosidase.

The presumed structure of the hybrid protein part obtained, at the level of fusion between the lac Z gene and the HBs-1 fragment results from FIG. 8F which shows the "β-gal" fragment, corresponding to β-galactosidase (1,005 amino acids), the HBsAg fragment (192 amino acids), these fragments being separated by a proline amino acid, corresponding to a part of "EcoRI linker" contained in the λlacHBs-1 vector.

C—PROCESS FOR MANUFACTURE OF AN IMMUNOGEN MOLECULE APPLYING THE VECTOR ACCORDING TO THE INVENTION

The invention can consequently permit the production of a protein of a molecular weight lower than the above-indicated polypeptides I or II, endowed with the same immunogenic properties.

The results show that E. coli, or any other suitable microorganism, such as a bacterium or a eucaryotic cell culture, can be infected by λlacHBs-1 and synthesize a protein having a molecular weight of the order of 138,000 and possessing determinants antigenic both of HBsAg and of β-galactosidase. This molecule is representative of the hybrid polypeptides, which can be obtained by the process according to the invention, in which HBsAg is connected to a support protein (resulting from the partial or total substitution of the β-galactosidase fragment), these hybrids possessing nonetheless the antigen properties of HBsAg. These novel molecules are useful for the production of vaccines active against viral hepatitis B.

As is self-evident, and as emerges already from the foregoing, the invention is in no way limited to those of its types of application and embodiments which have been more especially envisaged; it encompasses, on the contrary, all modifications.

Appended to this description is a bibliography, in particular of the references which have been cited within the scope of the present description.

REFERENCES

1—Blumberg, B. S. (1977) Science 197, 17–25.
2—Dane D. S., Cameron C. H., and Briggs M. (1970) Lancet 1, 695–698.
3—WHO Technical Report series, Number 602 (1976).
4—Summers J., O'Connel A., and Millman I. (1975) Proc. Nat. Acad. Sci. USA 72, 4597–4601.
5—Hruska J. F., Clayton D. A., Rubenstein J. L. R., and Robinson W. S. (1977) J. Virol. 21, 666–682.
6—Landers T. A., Greenberg H. B., and Robinson W. S. (1977) J. Virol. 23, 368–376.
7—Charnay P., Pourcel C., Louise A., Fritsch A., and Tiollais P. (1979) Proc. Nat. Acad. Sci. USA, 76 2222–2226.
8—Dreesman G. R., Hollinger F. B., Surians J. R., Fujioka R. B., Brunschwig J. P., and Melnick J. L. (1972) J. Virol. 10, 469–476.
9—Gerin J. L. (1974) in Mechanisms of virus disease Ed. W. S. Robinson, C. R. Fox pp. 215–24 Menlo Park: W.A. Benjamin.
10—Dreesman G. R., Chairez R., Suarez M., Hollinger F. B. Courtney R. J., and Melnick J. L. (1975) J. Virol. 16, 508–515.
11—Shih J. W. and Gerin J. L. (1977) J. Virol. 21, 1219–1222.
12—Peterson D. L., Roberts I. M., and Vyas G. N. (1977) Proc. Nat. Acad. Sci. USA 74, 1 530–1 534.
13—Peterson D. L., Chien D. Y., Vyas G. N., Nitecki D., and Bond H. (1978) in Viral Hepatitis, Ed. G. Vyas, S. Cohen and R. Schmid, The Franklin Institute Press, Philadelphia, 569–573.
14—Fritsch A., Pourcel C., Charnay P., and Tiollais P. (1978) C. R. Acad. Sc. Paris 287, 1453–1456.
15—Burrell C. J., Mackay P., Greenaway P. J., Hofschneider P. H., and Murray K. (1979) Nature 279 43–47.
16—Tiollais P., Perricaudet M., Petterson U., and Philipson L. (1976) Gene 1, 49–63.
17—Herisse J., Courtois G., and Galibert F. (1978) Gene 4, 279–294.
18—Kroeker W. D. and Laskowski M. S. R. (1977) Anal. Biochem. 79, 63–72.
19—Maxam A. M. and Gilbert W. (1977) Proc. Nat. Acad. Sci. USA 74, 560–564.
20—Sanger F., Nicklen S., and Coulson A. R. (1977) Proc. Nat. Acad. Sci. USA 74, 5463–5467.
21—Maat J. and Smith A. J. W. (1978) Nucleic Acid. Res. 5, 4537–4545.
22—Berget S. M., Moore C., and Sharp P. A. (1977) Proc. Nat. acad. Sci. USA 74, 3171–3175.
23—Chow L. T., Gelinas R. E., Broker T. R., and Roberts J. (1977), Cell 12, 1–8.
24—Shiraishi H., Kohama T., Shirachi R., and Ishida N. (1977) J. Gen. Virol. 36, 207–210.
25—Struck D. K., Lennarz W. J., and Brew K. (1978) J. Biol. Chem. 253, 5786–5794.
26—Reddy V. B., Thimmappaya B., Dhar R., Subramanian K. N. Zain B. S., Pan J., Celma C. L., and Weissman S. M. (1978) Science 200, 494–502.
27—Fiers W., Contreras R., Hargeman G., Roigers R., Van de Voorde A., Van Henverswyn H., Van Herreweghe J., Volchaerts G., and Ysebaert M. (1978) Nature 273, 113–117.
28—Sanger F., Air G. M., Barrell B. G., Brown N. L., Coulson A. R., Fiddes J. C., Hutchison III C. A., Slocombe P. M., and Smith M. (1977) Nature 265, 687–691.
29—Barrell B. G., Shaw D. C., Walker J. E., Northrop F. D., Godson G. N., and Fiddes J. C. (1978) Biochem. Soc. Trans. 6, 63–67.
30—Szmuness W., Am. J. Path. 81, 629–649 (1975).
31—Sninsky J. J., Siddiqui A., Robinson W. S., and Cohen S. N., Nature 279, 346–348 (1979).
32—Valenzuela P. et al., Nature 280, 815–819 (1979).
33—Charnay P. et al., Nucl. Acids Res. 7, 335–346 (1979).
34—Galibert F., Mandart E., Fitoussi F., Tiollais P., and Charnay P., Nature 281, 646–650 (1979).
35—Pasek M. et al., Nature 282, 575–579 (1979).
36—Byas G. N., Williams E. W., Klaus G. G. B., and Bond. H. J. Immunol 108, 1 114–1 118 (1972).
37—Hollinger F. B., Dressman G. R., Sanchez Y., Cabral G., and Melnick J. L., in Viral Hepatitis (Ed. Vyas G. N. Cohen S. N. and Schmid R.) Franklin Institute, Philadelphia, (1978).
38—Purcell R. H. and Gerin J. L., Am. J. Med. Sci. 270, 395–399 (1975).
39—Hilleman M. R. et al., Am. J. Med. Sci. 270, 401–404 (1975).
40—Maupas P., Coursaget P., Goudeau A., and Drucker J., Lancet 1, 1367–1370 (1976).
41—Emtage J. S. et al., Nature 283, 171–174 (1980).
42—Itakura K. et al., Science 198, 1056–1063 (1977).
43—Goeddel D. V. et al., Proc. Nat. Acad. Sci. USA 76, 106–110 (1979).
44—Pourcel C., Marchal C., Louise A., Fritsch A., and Tiollais P., Molec. Gen. Genet. 170, 161–169 (1979).
45—Bolivar F. et al., Gene 2, 95–113 (1977).
46—Fowler A. V. and Zabin I., Proc. Nat. Acad. Sci. USA 74, 1507–1510 (1977).
47—Laemmli U. K., Nature 227, 680–685 (1970).
48—Burgess R. R., J. Biol. Chem. 244, 6168–6176 (1969).
49—Bonner W. M. and Laskey R. A., Eur. J. Biochem. 45, 83–88 (1974).
50—Laskey R. A. and Mills A. D., Eur. J. Biochem. 56, 335–341 (1975).
51—Iwakura Y., Ito K., and Ishihama A., Molec. Gen. Genet. 133, 1–23 (1974).
52—Talwai G. P., et al., Proc. Nat. Acad. Sci. USA 73, 218–222 (1976).

We claim:

1. A phage or plasmid vector comprising double-stranded Hepatitis B virus DNA comprising monocatenary region of the Hepatitis B virus genome.

2. A phage or plasmid vector comprising double-stranded Hepatitis B virus DNA comprising monocatenary region of the Hepatitis B virus genome, wherein said monocatenary region is detectable by heteroduplex mapping.

3. A phage or plasmid vector comprising double-stranded Hepatitis B virus DNA comprising at least 150 base pairs of the monocatenary region of the Hepatitis B virus genome.

4. A phage or plasmid vector comprising double-stranded Hepatitis B virus DNA comprising at least 150 base pairs of the Hepatitis B virus genome.

* * * * *